US009759346B2

(12) United States Patent
Anderson

(10) Patent No.: US 9,759,346 B2
(45) Date of Patent: *Sep. 12, 2017

(54) METHODS AND APPARATUS FOR ANALYZING EFFECTS OF FRICTION ON PROCESS CONTROL DEVICES

(71) Applicant: Fisher Controls International LLC, Marshalltown, IA (US)

(72) Inventor: Shawn William Anderson, Haverhill, IA (US)

(73) Assignee: Fisher Controls International LLC, Marshalltown, IA (US)

( * ) Notice: Subject to any disclaimer, the term of this patent is extended or adjusted under 35 U.S.C. 154(b) by 206 days.

This patent is subject to a terminal disclaimer.

(21) Appl. No.: 14/733,806

(22) Filed: Jun. 8, 2015

(65) Prior Publication Data

US 2015/0267839 A1   Sep. 24, 2015

Related U.S. Application Data

(63) Continuation of application No. 13/451,862, filed on Apr. 20, 2012, now Pat. No. 9,092,019.

(51) Int. Cl.
*G01N 19/02* (2006.01)
*F16K 37/00* (2006.01)
(Continued)

(52) U.S. Cl.
CPC ......... *F16K 37/0083* (2013.01); *G01N 19/02* (2013.01); *G05B 15/02* (2013.01); *G05B 23/0283* (2013.01)

(58) Field of Classification Search
None
See application file for complete search history.

(56) References Cited

U.S. PATENT DOCUMENTS 4,029,122 A * 6/1977 Jaegtnes ............. F16K 37/0083
137/551
4,694,390 A * 9/1987 Lee ..................... G05B 19/358
137/487.5
(Continued)

FOREIGN PATENT DOCUMENTS

DE    102005004477    8/2006

OTHER PUBLICATIONS

International Searching Authority, "International Search Report," issued in connection with PCT Application No. PCT/US2013/037134, mailed on May 21, 2014, 2 pages.
(Continued)

*Primary Examiner* — Paul West
*Assistant Examiner* — Mark A Shabman
(74) *Attorney, Agent, or Firm* — Hanley, Flight & Zimmerman, LLC

(57) ABSTRACT

Methods and apparatus for analyzing effects of friction on process control devices are disclosed herein. An example apparatus includes a housing; a processor disposed in the housing, the processor to: determine a first force or torque corresponding to friction of a process control device and an actuator operatively coupled to the process control device via a stem or shaft; in response to the first force or torque, determine a first command to operate the process control device via the stem or shaft to obtain a first response of the actuator; determine a second force or torque corresponding to friction of the process control device and the actuator; and in response to the second force or torque, determine a second command to operate the process control device via the stem or shaft to obtain a second response of the actuator.

15 Claims, 4 Drawing Sheets

(51) Int. Cl.
*G05B 15/02* (2006.01)
*G05B 23/02* (2006.01)

(56) References Cited

U.S. PATENT DOCUMENTS

| | | | | | |
|---|---|---|---|---|---|
| 5,424,941 | A | * | 6/1995 | Bolt | G05B 19/358 137/625.65 |
| 5,644,948 | A | | 7/1997 | Karte et al. | |
| 6,056,008 | A | * | 5/2000 | Adams | G05D 16/2093 137/487.5 |
| 6,745,084 | B2 | * | 6/2004 | Boger | F15B 5/006 700/13 |
| 7,039,537 | B2 | * | 5/2006 | Junk | G05B 23/0229 702/182 |
| 7,089,086 | B2 | * | 8/2006 | Schoonover | G05B 17/02 251/129.01 |
| 7,539,560 | B2 | * | 5/2009 | Boger | F15B 5/006 137/12 |
| 7,584,643 | B2 | | 9/2009 | Hoffman | |
| 2006/0185418 | A1 | * | 8/2006 | Hoffman | G05B 23/0256 73/1.72 |
| 2009/0222124 | A1 | | 9/2009 | Latwesen | |
| 2010/0147395 | A1 | * | 6/2010 | Meier | F16K 31/1262 137/14 |
| 2010/0152907 | A1 | * | 6/2010 | Meier | F16K 37/0091 700/282 |
| 2010/0176320 | A1 | * | 7/2010 | Kresse | F16K 31/1262 251/129.04 |
| 2013/0276511 | A1 | | 10/2013 | Anderson | |

OTHER PUBLICATIONS

International Searching Authority, "Written Opinion," issued in connection with PCT Application No. PCT/US2013/037134, mailed on May 21, 2014, 8 pages.
International Searching Authority, "International Preliminary Report on Patentability," issued in connection with PCT Application No. PCT/US2013/037134, mailed on Oct. 21, 2014, 9 pages.
United States Patent and Trademark Office, "Restriction," issued in connection with U.S. Appl. No. 13/451,862, mailed on Mar. 17, 2014, 6 pages.
United States Patent and Trademark Office, "Non-Final Office Action," issued in connection with U.S. Appl. No. 13/451,862, mailed on May 23, 2014, 11 pages.
United States Patent and Trademark Office, "Final Office Action," issued in connection with U.S. Appl. No. 13/451,862, mailed on Oct. 21, 2014, 14 pages.
United States Patent and Trademark Office, "Notice of Allowance," issued in connection with U.S. Appl. No. 13/451,862, mailed on Mar. 19, 2015, 20 pages.

* cited by examiner

METHODS AND APPARATUS FOR ANALYZING EFFECTS OF FRICTION ON PROCESS CONTROL DEVICES

RELATED APPLICATION

This patent arises from a continuation of U.S. patent application Ser. No. 13/451,862, filed on Apr. 20, 2012, which is hereby incorporated herein by reference in its entirety.

FIELD OF THE DISCLOSURE

This disclosure relates generally to process control devices and, more particularly, to methods and apparatus for analyzing effects of friction on process control devices.

BACKGROUND

Process control systems generally use a variety of process control devices (e.g., rotary valves, linear valves, etc.) to control a process. The process control devices are often operated by an actuator via a stem or shaft. During operation, friction of the process control device and the actuator resists movement of the stem or shaft. Over time, the friction of the process control device and the actuator may increase or decrease.

SUMMARY

An example apparatus includes a housing; a processor disposed in the housing, the processor to: determine a first force or torque corresponding to friction of a process control device and an actuator operatively coupled to the process control device via a stem or shaft; in response to the first force or torque, determine a first command to operate the process control device via the stem or shaft to obtain a first response of the actuator; determine a second force or torque corresponding to friction of the process control device and the actuator; and in response to the second force or torque, determine a second command to operate the process control device via the stem or shaft to obtain a second response of the actuator.

DETAILED DESCRIPTION

Figure 1:
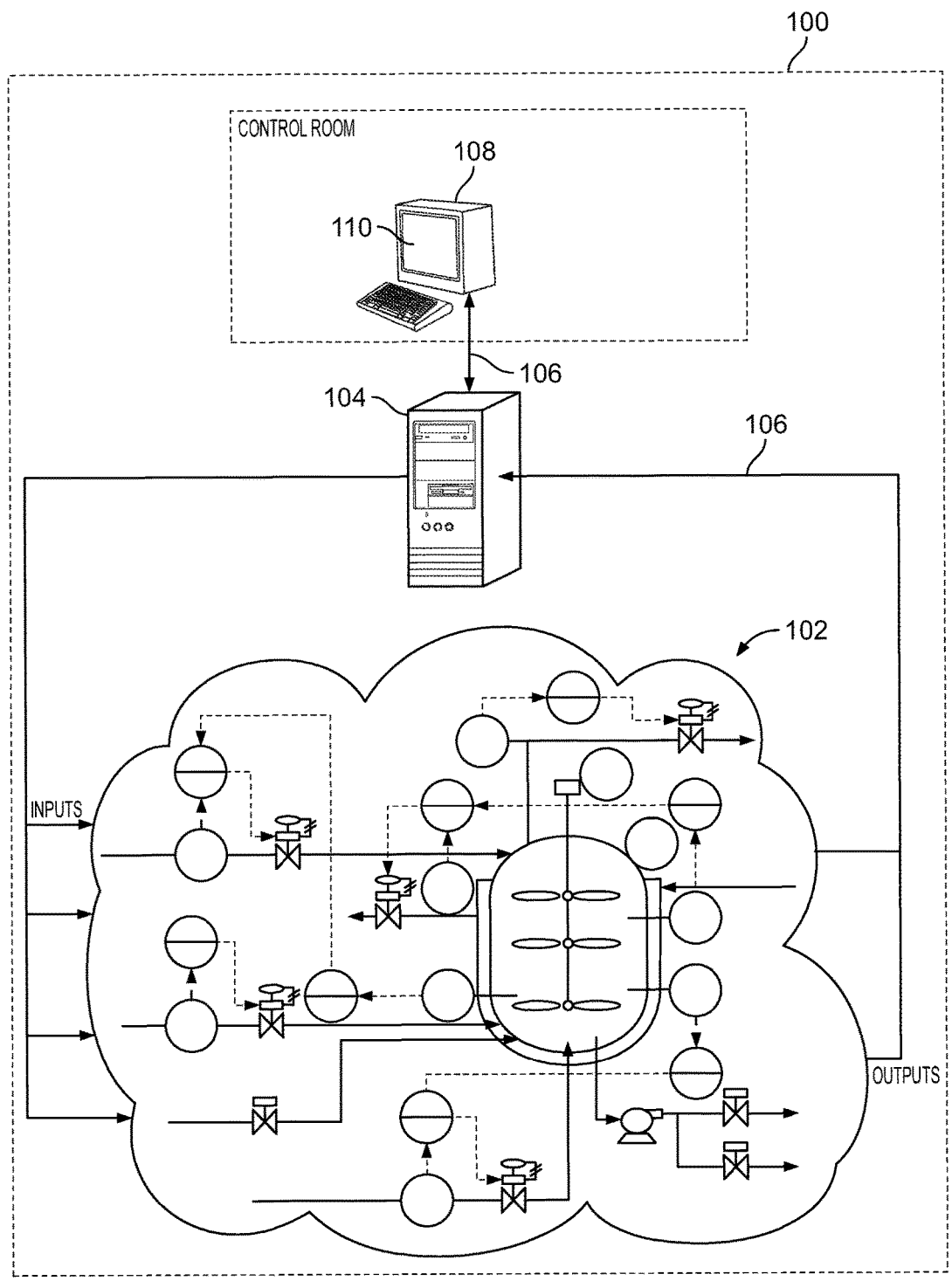
FIG. 1 illustrates an example process control system within which the teachings of this disclosure may be implemented.

While the following example apparatus and methods are described in conjunction with a linear valve and a linear actuator, the example apparatus and methods may also be used with any other process control device operated by a linear or rotary actuator such as, for example, throttle valves, isolation valves, rotary valves, and/or any other process control device.

Industrial processes (e.g., oil and gas distribution systems, chemical processing plants, etc.) are often controlled by a variety of process control devices (e.g., linear valves, rotary valves, throttle valves, isolation valves, etc.). A process control device is often operated by an actuator via a stem or shaft. The actuator provides a force or torque to the stem or shaft to move a flow control member (e.g., a plug, a disk, a ball, etc.) of the process control device. During operation, fluid flows through the process control device and subjects the flow control member and, thus, the stem or shaft to a variety of forces. Also, during operation, friction of the process control device and the actuator resists movement of the stem or shaft. If the friction increases, an amount of movement of the stem or shaft in response to a given amount of force of torque of the actuator may vary between operational cycles, the movement may be sluggish, or the stem or shaft may not move in response to the force or torque provided by the actuator. If the friction decreases, the amount of movement of the stem or shaft in response to a given amount force or torque of the actuator may increase.

The examples disclosed herein may be used to analyze or assess an effect of friction on operation of a process control device operated by an actuator. In some examples, the effect of the friction on the operation of the process control device is exhibited as a deterioration of a movement characteristic of a stem or shaft of the actuator, which may be indicative of an impairment or disability of the process control device or the actuator (e.g., wear of a seal, inadequate supply air pressure to the actuator, blockage of a flow path of the process control device, etc).

An example method disclosed herein includes determining a value corresponding to friction of the actuator and the process control device operated by the actuator. In some examples, the value corresponding to the friction is a difference between a force or torque applied by the actuator to the stem or shaft at a first position and a force or torque applied by the actuator to the stem or shaft at a second position during movement of the stem from the first position to the second position (i.e., a differential force corresponding to dynamic friction opposing the movement of the stem from the first position to the second position). The example method further includes determining a value indicative of an effect of the friction on operation of the process control device via the actuator based on the value corresponding to the friction and a predetermined value.

The effect of the friction on the operation of the process control device may correspond to a movement characteristic of the stem or shaft of the process control device such as, for example, a sensitivity, a preciseness, and/or a responsiveness of movement of the stem or shaft in response to a force or torque applied by the actuator to the stem or shaft. In some examples, the predetermined value is a difference between a maximum force or torque of the actuator and a force or torque of the actuator to perform an action. To determine the value indicative of the effect of the friction, the value corresponding to the friction may be compared to the predetermined value using, for example, a ratio. An alert message may be sent when the ratio indicates that the effect of the friction has reached a predetermined level.

FIG. 1 illustrates an example process control system 100 that may be used to implement the example apparatus and methods disclosed herein. The example process control system 100 includes any number of process control devices 102 such as input devices and/or output devices. In some examples, the input devices include valves, pumps, fans, heaters, coolers, mixers, and/or other devices, and the output devices include thermometers, pressure gauges, concentration gauges, fluid level meters, flow meters, vapor sensors, valve controllers, and/or other devices. The input and output devices are communicatively coupled to a controller 104 (e.g., a DeltaV™ controller) via a data bus (e.g., Foundation Fieldbus™ and HART™) or local area network (LAN) 106. The input and output devices may be wirelessly communicatively coupled to the controller 104. The controller 104 transmits instructions to the input devices to control the process and receives and/or collects information (e.g., measured process information, environmental information, and/or input device information, etc.) transmitted by the output devices. The controller 104 generates notifications, alert messages, and/or other information. The controller 104 is also communicatively coupled to a workstation 108, which includes an interface 110 that displays process control information (e.g., measured process control information, alert message, etc.). Although a single controller 104 is shown in FIG. 1, one or more additional controllers may be included in the example system 100 without departing from the teachings of this disclosure.

Figure 2:
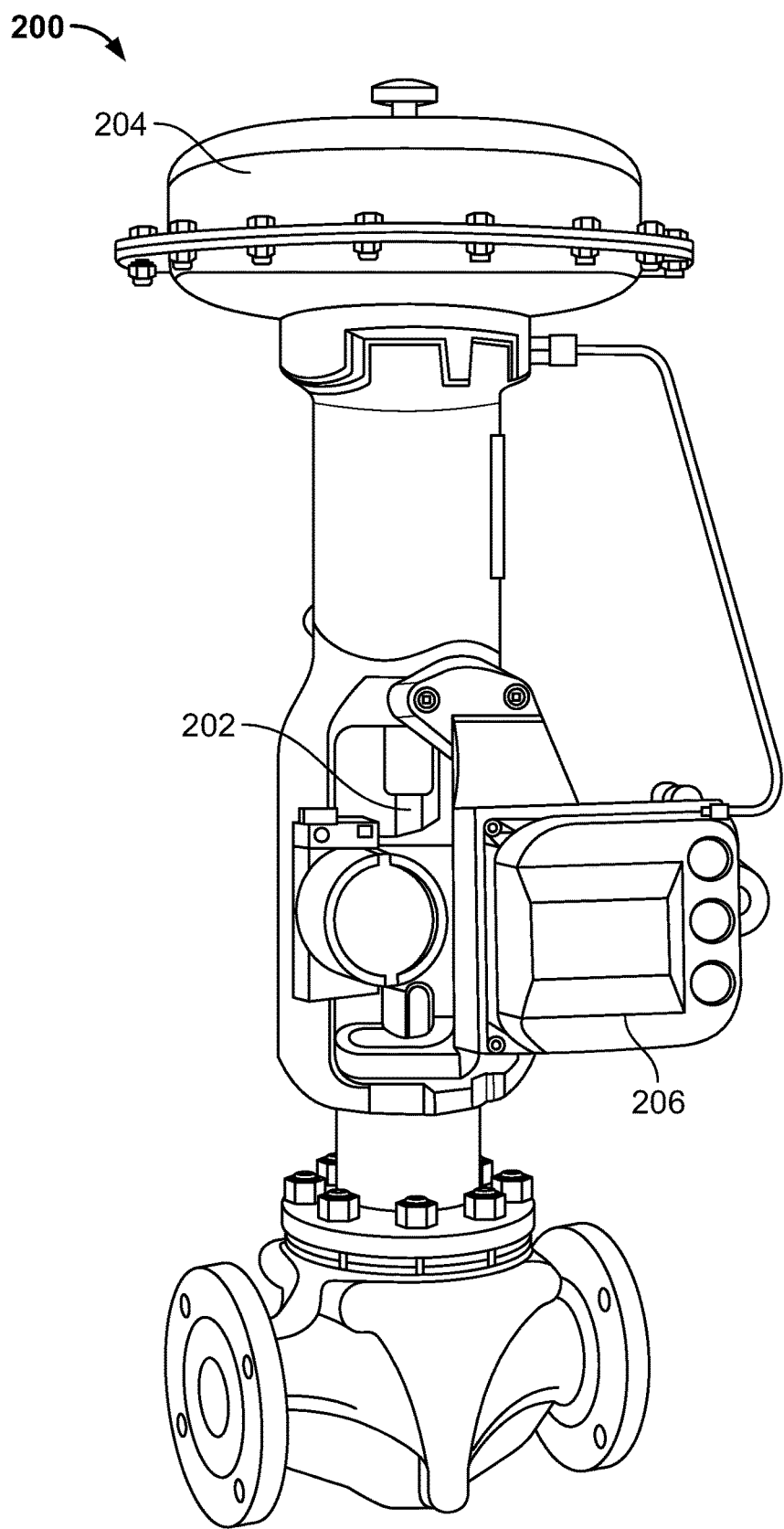
FIG. 2 depicts an example process control device that may be used to implement example methods disclosed herein.

FIG. 2 depicts an example process control device 200 that may be used to implement the examples disclosed herein. The example process control device 200 depicted in FIG. 2 is a linear valve (e.g., a Fisher® ED Valve). However, other process control devices such as, for example, rotary valves (e.g., a Fisher® Vee-Ball™ V150 valve, a Fisher® Vee-Ball™ V300 valve, etc.), throttle valves, isolation valves, and/or other process control devices may be used to implement the examples disclosed herein. The example process control device 200 includes a flow control member (not shown) (e.g., a plug, a disk, a ball, etc.) coupled to a stem 202. A linear actuator 204 (e.g., Fisher® 667 Actuator) is operatively coupled to the stem 202 to move the stem 202 during operation. Some example process control devices that may be used to implement the examples disclosed herein include a rotary valve or other device operatively coupled to a rotary actuator. In the illustrated example, the actuator 204 is a pneumatic actuator. However, other actuators such as, for example, electric or hydraulic actuators may be used to implement the examples disclosed herein. An estimated maximum force or torque of the actuator 204 may be determined based on characteristics of the actuator 204 and the process control system 100 such as, for example, an air supply pressure available, an effective area of the actuator 204, a lever arm length and/or other characteristics. The example process control device 200 also includes a seal (not shown).

In the illustrated example, the process control device 200 includes a digital valve controller 206 ("DVC") (e.g., Fisher® FIELDVUE™ DVC6200 Digital Valve Controller) to collect information such as, for example, a position of the stem 202, a direction of stem travel, a count of operational cycles, actuator pressures, a force or torque provided by the actuator 204 and/or other information. The DVC 206 is communicatively coupled to the actuator 204 and the controller 104. During operation, the DVC 206 transmits the information to the controller 104 and receives information from the controller 104. Based on the information, the DVC 206 transmits commands to the actuator 204 (e.g., via a pneumatic signal).

In response to a command from the DVC 206, the actuator 204 applies a force to the stem 202 to perform an action (e.g., move the flow control member, sealingly engage or disengage the flow control member and a seat, etc.). Friction of the process control device 200 and the actuator 204 resists movement of the stem 202. Factors affecting the amount of friction include, for example, valve design, actuator effective area, valve port size, trim unbalance area, stem size, shutoff classification of the valve, valve seat type, and/or other factors. Process conditions (e.g., valve inlet pressure, valve outlet pressure, direction of fluid flow, etc.) may also resist or encourage the movement of the stem 202.

Thus, when the process control device 200 is online (i.e., being used to control the process), the force applied to the stem 202 to perform the action is a sum or net force needed to overcome the friction of the process control device 200 and the actuator 204; a force on the stem 202 caused by the process conditions; and any additional forces to perform the action (e.g., a force to compress an actuator spring, a force to achieve a desired shutoff classification, etc.). An estimated force of the actuator 204 needed to perform the action may be determined based on estimated process conditions (e.g., estimated valve inlet pressure, estimated valve outlet pressure, etc.) and/or characteristics of the action such as, for example, shutoff classification desired, stem travel distance, etc.

Friction affects operation of the process control device 200 via the actuator 204. More specifically, over time the friction of the process control device 200 and/or the actuator 204 may increase or decrease due to, for example, wear, flow path blockages, process media accumulation, etc. As a result, movement characteristics of the stem 202 in response to forces applied to the stem 202 by the actuator 204 may change or deteriorate, thereby affecting a response of the actuator 204 and, thus, the process control device 200 to a command to operate the process control device 200 via the stem 202. Further, a range of suitable controller tuning speeds may decrease.

In some examples, one of the movement characteristics affected by the friction of the process control device 200 and the actuator 204 is a sensitivity of movement of the stem 202. In such examples, if the friction increases, a force to move the stem 202 a first distance may increase during subsequent operational cycles. For example, at a first amount of friction, the stem 202 may move the first distance only when the actuator 204 provides at least a first amount of force. After a plurality of operational cycles (e.g., 10,000), the friction of the process control device 200 and the actuator 204 may increase to a second amount of friction, and the stem 202 may move the first distance only when the actuator 204 provides at least a second amount of force that is greater than the first amount of force to the stem 202. In some examples, a minimum increment of travel of the stem 202 in response to the given force provided by the actuator 204 increases for subsequent operational cycles as the friction increases. For example, the stem 202 may move in increments only as small as, for example, a distance corresponding to 0.25 percent of total possible travel or span at the first amount of friction. However, at the second amount of friction, the stem 202 may move in increments only as small as, for example, a distance corresponding to two percent of total possible travel.

In some examples, one of the movement characteristics affected by the friction of the process control device 200 and the actuator 204 is a preciseness of the movement of the stem 202. In such examples, an amount of movement traveled by the stem 202 in response to the force provided by the actuator 204 may vary or become more variable as the friction increases. For example, at the first amount of friction, the stem 202 may move a distance of about 0.50 inches in response to the first amount of force applied to the stem 202 by the actuator 204. However, if the friction increases to the second amount of friction that is greater than the first amount of friction, the amount of movement of the stem 202 may vary between, for example, about 0.35 inches and 0.50 inches in response the first amount of force for subsequent operational cycles.

In some examples, one of the movement characteristics affected by the friction of the process control device 200 and the actuator 204 is a responsiveness of movement of the stem 202. In such examples, as the friction increases, a time to initially move the stem 202 in response to the force provided to the stem 202 by the actuator 204 increases during subsequent operational cycles. For example, at the first amount of friction, the stem 202 may initially move a first amount of time after the first amount of force is applied to the stem 202. At the second amount of friction, the stem 202 may initially move a second amount of time that is greater than the first amount of time after the first amount of force is applied to the stem 202. In some examples, when the friction increases from the first amount of friction to the second amount of friction, a time to move the stem 202 over a distance (e.g., an inch) increases (i.e., the stem 202 moves slower) when, for example, the first amount of force is applied to the stem 202.

Figure 3:
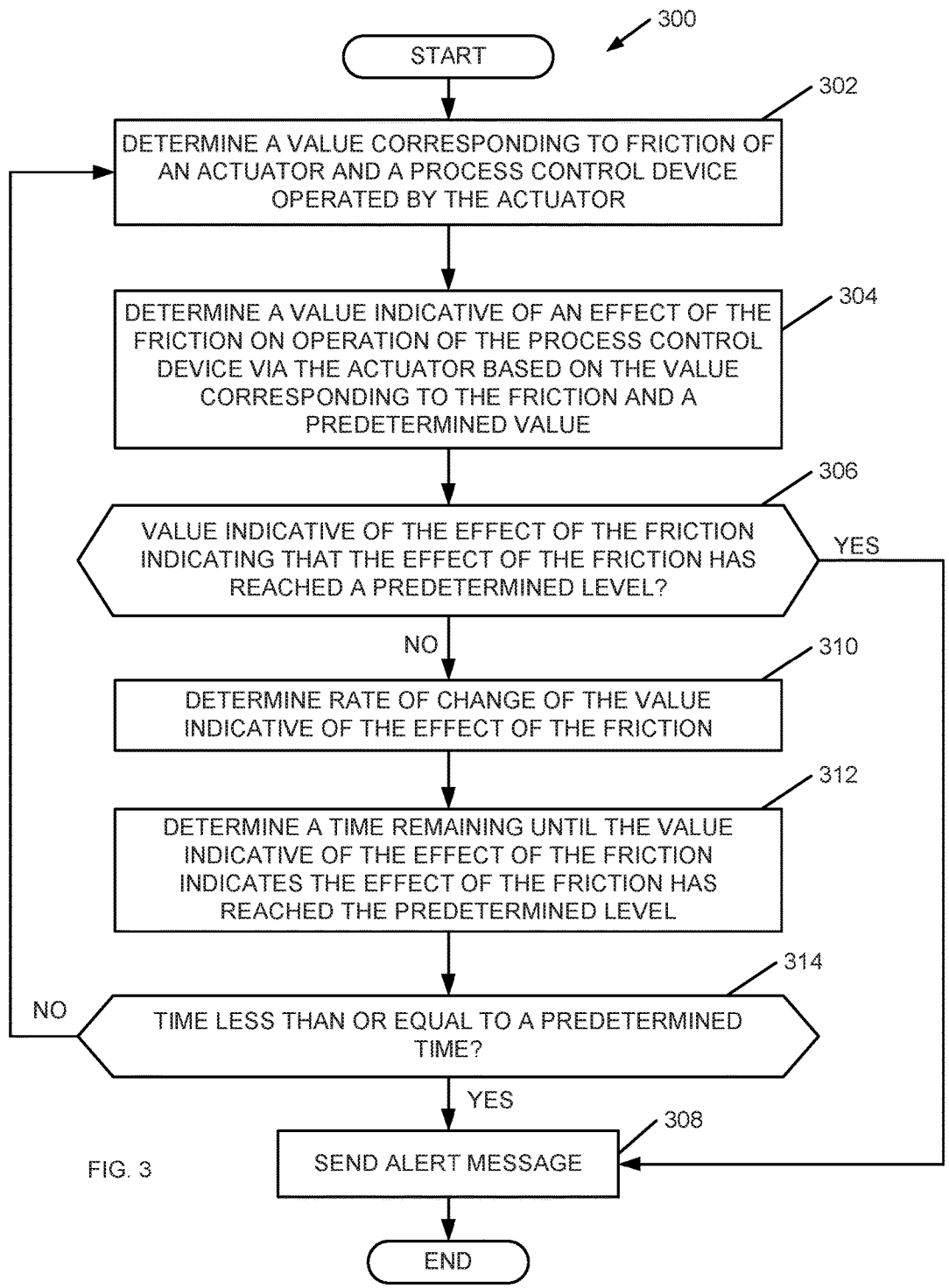
FIG. 3 is a flow chart representative of an example method disclosed herein.
Figure 4:
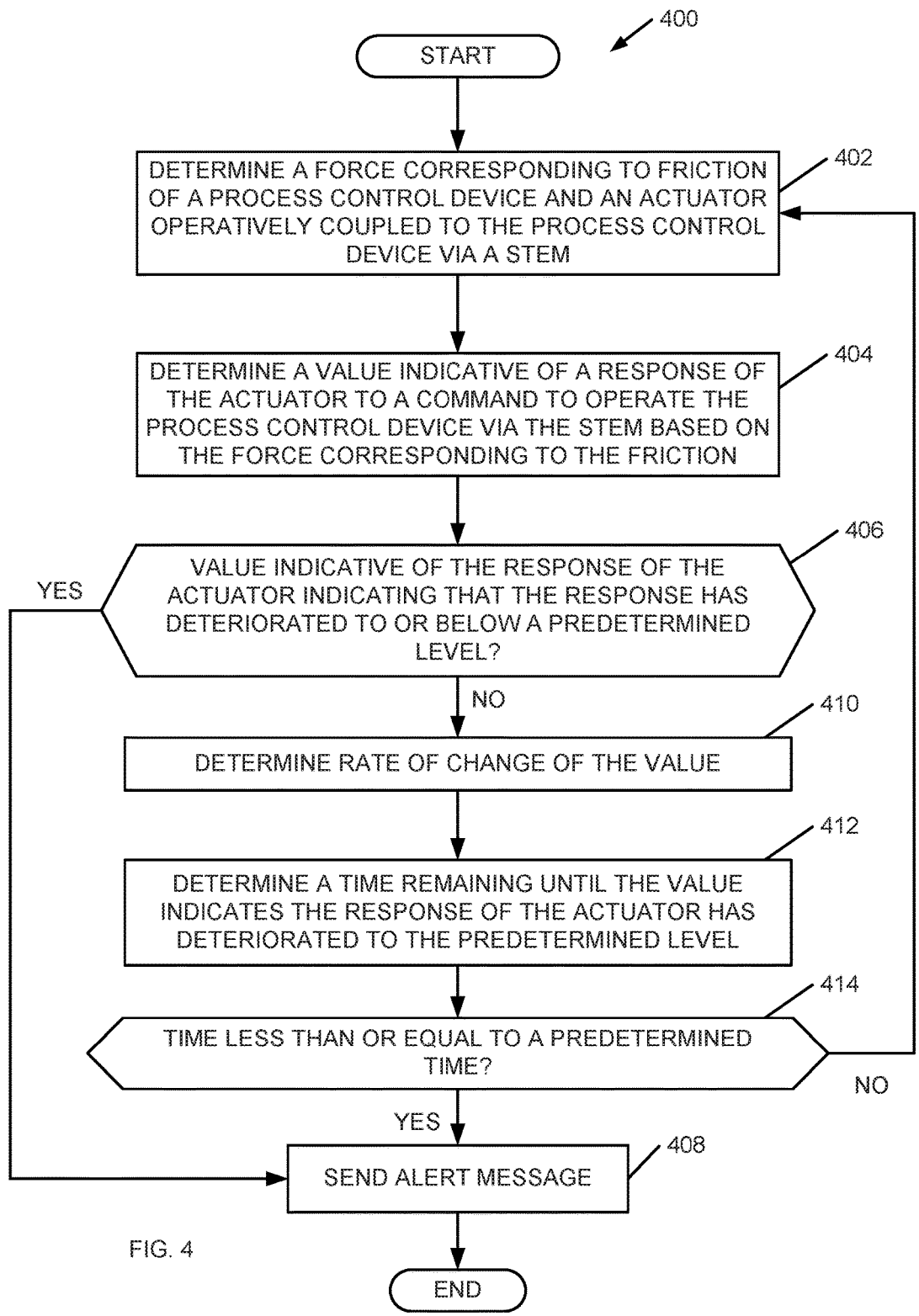
FIG. 4 is a flow chart representative of another example method disclosed herein.

FIGS. 3-4 are flowcharts representative of example methods disclosed herein. Some or all of the example methods of FIGS. 3-4 may be carried out by a processor, the controller 104 and/or any other suitable processing device. In some examples, some or all of the example methods of FIGS. 3-4 are embodied in coded instructions stored on a tangible machine accessible or readable medium such as a flash memory, a ROM and/or random-access memory RAM associated with a processor. Alternatively, some or all of the example methods of FIGS. 3-4 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, one or more of the operations depicted in FIGS. 3-4 may be implemented manually or as any combination of any of the foregoing techniques, for example, any combination of firmware, software, discrete logic and/or hardware. Further, although the example methods are described in reference to the flowcharts illustrated in FIGS. 3-4, many other methods of implementing the example methods may be employed. For example, the order of execution of the blocks may be changed, and/or some of the blocks described may be changed, eliminated, subdivided, or combined. Additionally any or all of the example methods of FIGS. 3-4 may be carried out sequentially and/or carried out in parallel by, for example, separate processing threads, processors, devices, discrete logic, circuits, etc.

While the following example methods of FIGS. 3-4 are described in conjunction with a linear valve and a linear actuator 204, other example methods may be implemented using any other process control device operated by a linear actuator or a rotary actuator such as, for example, throttle valves, isolation valves, rotary valves, and/or any other process control device.

With reference to FIGS. 1 and 2, the example method or process 300 of FIG. 3 begins by determining a value corresponding to friction of the actuator 204 and the process control device 200 operated by the actuator 204 (block 302). In some examples, determining the value corresponding to the friction includes determining a difference between a force applied to the stem 202 by the actuator 204 at a first position and a force applied to the stem 202 by the actuator 204 at a second position during movement of the stem 202 from the first position to the second position. The first and second forces provided by the actuator 204 may be determined by the DVC 206 when the process control device 200 is online or offline.

At block 304, a value indicative of an effect of the friction on operation of the process control device 200 via the actuator 204 is determined based on the value corresponding to the friction and a predetermined value. In some examples, the effect of the friction on the operation of the process control device 200 is a change or deterioration of a movement characteristic of the stem 202 in response to a force applied by the actuator 204 to the stem 202. For example, to operate the process control device 200, the DVC 206 sends a command to the actuator 204 (e.g., via a pneumatic signal), which provides the force to the stem 202 based on the command. The movement characteristic may be a sensitivity, a preciseness, or a responsiveness of movement of the stem 202 in response to the force provided by the actuator 204. If the friction increases or decreases during operation, the effect of the friction on the operation may be an increase or a decrease of the sensitivity, the preciseness, and/or the responsiveness of the movement of the stem 202 in response to the force provided by the actuator 204.

In the illustrated example, the predetermined value is an estimated force. In some examples implemented using a rotary actuator, the predetermined value is an estimated torque. The estimated force or torque may be a difference between an estimated maximum force or torque of the actuator 204 and an estimated force or torque of the actuator 204 to perform an action (e.g., move the flow control member, sealingly engage or disengage the flow control member and a seal, etc.). The estimated maximum force or torque of the actuator 204 is determined based on characteristics of the actuator 204, the stem 202 and/or the process control system 100 such as, for example, a supply pressure available, an actuator effective area, a lever arm length, a maximum shear strength of the stem 202 and/or other characteristics. The estimated force or torque of the actuator 204 to perform the action may be determined based on estimated process conditions (e.g., estimated valve inlet pressure, estimated valve outlet pressure) and/or characteristics of the action such as, for example, shutoff classification desired, stem travel distance, etc.

The value indicative of the effect of the friction on the operation of the process control device 200 may be determined by comparing the value corresponding to the friction to the estimated force via, for example, a ratio. The ratio of the estimated force over the value corresponding to the friction may equal, for example, 15, which may indicate that the stem 202 moves a distance corresponding to 0.25 percent of total possible stem travel in response to the first amount of force applied to the stem 202 via the actuator 204. However, if the ratio subsequently equals 5, the ratio may indicate that the movement characteristic has deteriorated. For example, the ratio equaling 5 may indicate that the stem 202 moves the distance corresponding to 0.25 percent of total possible stem travel in response to the second amount of force that is greater than the first amount of force.

At block 306, it is determined whether the value indicative of the effect of the friction indicates that the effect of the friction has reached a predetermined level. For example, the predetermined level may be indicated by the ratio being less than or equal to 15. If the value indicates that the effect of the friction has reached the predetermined level, then an alert message is sent (block 308). For example, the DVC 206 and/or the controller 104 generates and sends the alert message to the workstation 108 if the ratio equals 15 or less.

If the value indicates the effect of the friction has not reached the predetermined level, then a rate of change of the value indicative of the effect of the friction is determined (block 310). In some examples, determining the rate of change of the value indicative of the effect of the friction is based on the value indicative of the effect of the friction determined at block 304 and one or more values indicative of the effect of the friction. For example, during operation, the process control device 200 may undergo a plurality of operational cycles in which the actuator 204 operates the process control device 200 via the stem 202 (e.g., outputs a force to move the stem 202). The DVC 206 and/or the controller 104 may determine and/or log in a table or database a frequency of the force outputs and a value indicative of the effect of the friction corresponding to the force output for each of the operational cycles. If, at block 306, the value indicates the effect of the friction determined at block 304 has not reached the predetermined level then, at block 310, the frequency, the value determined at block 304, and the values from the table or database may be used to determine the rate of change of the value indicative of the effect of the friction. For example, corresponding to force outputs over about a five hour period of time, the values from the table or database may be 18.5, 18.4, 18.3, and 18.15 and the value determined at block 304 may be 18.0. As a result, the DVC 206 or the controller 104 determines that the frequency of the force outputs is 1 per hour and the rate of change of the value is, thus, about 0.1 per hour.

Based on the rate of change and the value indicative of the effect of the friction, a time remaining until the value indicates the effect of the friction has reached the predetermined level is determined (block 312). For example, if the value is 18, the rate of change of the value is 0.1 per hour and the predetermined level is indicated by the value equaling 15, then the time remaining until the value indicates the effect of the friction has reached the predetermined level is 30 hours.

At block 314, whether the time is less than or equal to a predetermined time is determined. If the time is greater than the predetermined time, the example method 300 returns to block 302. If the time is equal to or less than the predetermined time, an alert message is sent (block 308). For example, the DVC 206 and/or the controller 104 generates and sends an alert message to the workstation 108 if the time is equal to or less than one day and/or any other suitable time.

FIG. 4 is a flowchart representative of another example method disclosed herein. With reference to FIGS. 1 and 2, the example method or process 400 of FIG. 4 begins by determining a value corresponding to friction of the process control device 200 and the actuator 204, which is operatively coupled to the process control device 200 via the stem 202 (block 402). In some examples, determining the value corresponding to the friction includes determining a difference between a force applied to the stem 202 by the actuator 204 at a first position and a force applied to the stem 202 by the actuator 204 at a second position during movement of the stem 202 from the first position to the second position. The first and second forces provided by the actuator 204 may be determined by the DVC 206 when the process control device 200 is online or offline.

At block 404, based on the force corresponding to the friction, a value indicative of a response of the actuator 204 to a command to operate the process control device 200 via the stem 202 is determined. In some examples, the value indicative of the response of the actuator corresponds to a movement characteristic of the stem 202 in response to a force applied by the actuator 204 to the stem 202. The movement characteristic may be a sensitivity, a preciseness, or a responsiveness of movement of the stem 202. For example, the DVC 206 sends the command to the actuator 204 (e.g., via a pneumatic signal) to operate the process control device 200. Based on the command, the actuator 204 applies the force to the stem. If the friction increases or decreases during operation, the sensitivity, the preciseness, and/or the responsiveness of the stem 202 may increase or decrease in response to the force applied by the actuator 204 to the stem 202. As a result, the response of the actuator 204 to the command to operate the process control device 200 may change or deteriorate. For example, if the friction increases, the force to move the stem 202 via the actuator 204 to a commanded position may increase.

In some examples, determining the value indicative of the response of the actuator 204 includes comparing the force corresponding to the friction to an estimated force or torque. The estimated force or torque may be a difference between an estimated maximum force or torque of the actuator 204 and an estimated force or torque of the actuator 204 to perform an action (e.g., move the flow control member, sealingly engage or disengage the flow control member and a seal, etc.). The estimated maximum force or torque of the actuator 204 is determined based on characteristics of the actuator 204, the stem 202 and/or the process control system 100 such as, for example, a supply pressure available, an actuator effective area, a lever arm length, a maximum shear strength of the stem 202 and/or other characteristics. The estimated force or torque of the actuator 204 to perform the action may be determined based on estimated process conditions (e.g., estimated valve inlet pressure, estimated valve outlet pressure) and/or characteristics of the action such as, for example, shutoff classification desired, stem travel distance, etc.

In some examples, the force corresponding to the friction is compared to the estimated force using a ratio. For example, the ratio of the estimated force over the value corresponding to the friction may equal, for example, 15, which may indicate that the actuator 204 responds to a command to move the stem 202 a distance corresponding to 0.25 percent of total possible stem travel by applying the first amount of force. However, if the ratio subsequently equals 5, the ratio may indicate that the response of the actuator 204 has deteriorated. For example, the ratio equaling 5 may indicate that the friction of the actuator 204 and/or the process control device 200 increased, and the actuator 204 responds to the command to move the stem 202 the distance corresponding to 0.25 percent of the total possible stem travel by applying the second amount of force that is greater than the first amount of force to the stem 202.

At block 406, it is determined whether the value indicative of the response of the actuator 204 indicates that the response of the actuator 204 has deteriorated to or below a predetermined level. For example, the predetermined level may be indicated by the ratio equaling 15. If the value indicates that the response of the actuator 204 has deteriorated to or below the predetermined level, then an alert message is sent (block 408). For example, the DVC 206 and/or the controller 104 generates and sends the alert message to the workstation 108 if the ratio equals 15 or less.

If the value indicates the response of the actuator 204 has not deteriorated to or below the predetermined level, then a rate of change of the value indicative of the response of the actuator 204 is determined (block 410). In some examples, determining the rate of change of the value indicative of the response of the actuator 204 is based on the value indicative of the response of the actuator 204 determined at block 404 and one or more values indicative of the response of the actuator 204. For example, during operation, the process control device 200 may undergo a plurality of operational cycles in which the actuator 204 outputs a force to the stem 202. The DVC 206 and/or the controller 104 may determine and/or log in a table or database a frequency of the force outputs and a value indicative of the response of the actuator 204 corresponding to the force output for each of the operational cycles. If, at block 406, the value indicates the response of the actuator 204 determined at block 404 has not deteriorated to or below the predetermined level then, at block 410, the frequency, the value determined at block 404, and the values from the table or database may be used to determine the rate of change of the value indicative of the response of the actuator 204. For example, corresponding to force outputs over about a five hour period of time, the values from the table or database may be 16.5, 16.4, 16.3, and 16.15 and the value determined at block 404 may be 16.0. As a result, the DVC 206 or the controller 104 determines that the frequency of the force outputs is 1 per hour and the rate of change of the value is, thus, about 0.1 per hour.

Based on the rate of change and the value indicative of the response of the actuator 204 determined at block 404, a time remaining until the value indicates the response of the actuator 204 has deteriorated to or below the predetermined level is determined (block 412). For example, if the value is 16, the rate of change of the value is 0.1 per hour and the predetermined level is indicated by the value equaling 15, then the time remaining until the value indicates the response of the actuator 204 has deteriorated to the predetermined level is 10 hours.

At block 414, whether the time is less than or equal to a predetermined time is determined. If the time is greater than the predetermined time, the example method 400 returns to block 402. If the time is equal to or less than the predetermined time, the alert message is sent (block 408). For example, the DVC 206 and/or the controller 104 generates and sends the alert message to the workstation 108 if the time is equal to or less than one day and/or any other suitable time.

An example method includes determining a force or torque corresponding to friction of a process control device and an actuator operatively coupled to the process control device via a stem or shaft; and determining a value indicative of a response of the actuator to a command to operate the process control device via the stem or shaft based on the force or torque corresponding to the friction. In some examples, determining the value indicative of the response of the actuator includes comparing the force or torque corresponding to the friction to an estimated force or torque. In some examples, the estimated force or torque is based on a difference between an estimated maximum force or torque of the actuator and an estimated force or torque of the actuator to perform an action. In some examples, the value indicative of the response of the actuator corresponds to a movement characteristic of the stem or shaft in response to a force or torque applied to the stem or shaft by the actuator. In some examples, the movement characteristic is a sensitivity. In some examples, the movement characteristic is a preciseness. In some examples, the movement characteristic is a responsiveness. In some examples, the method includes sending an alert message when the value indicates the response of the actuator has deteriorated to or below a predetermined level. In some examples, determining the force or torque corresponding to the friction includes determining a difference between a force or torque applied by the actuator to the stem or shaft at a first position and a force or torque applied by the actuator to the stem or shaft at a second position during movement of the stem or shaft from the first position to the second position.

An example method includes determining a value corresponding to friction of an actuator and a process control device to be operated by the actuator; and determining a value indicative of an effect of the friction on operation of the process control device via the actuator based on the value corresponding to the friction and a predetermined value. In some examples, determining the value corresponding to the friction includes determining a difference between a force or torque applied by the actuator to the stem or shaft at a first position and a force or torque applied by the actuator to the stem or shaft at a second position during movement of the stem or shaft from the first position to the second position. In some examples, the effect of the friction on the operation of the process control device is an increase or decrease of a sensitivity of movement of a stem or shaft of the process control device in response to a force or torque applied by the actuator to the stem or shaft. In some examples, the effect of the friction on the operation of the process control device is a decrease of a preciseness of movement of a stem or shaft of the process control device in response to a force or torque applied by the actuator to the stem or shaft. In some examples, the effect of the friction on the operation of the process control device is an increase or decrease of a responsiveness of movement of a stem or shaft of the process control device in response to a force or torque applied by the actuator to the stem or shaft. In some examples, the predetermined value is a difference between a maximum force or torque of the actuator and a force or torque of the actuator to perform an action. In some examples, the method includes sending an alert message when the value indicative of the effect of the friction indicates the effect of the friction has reached a predetermined level. In some examples, the method includes determining a rate of change of the value indicative of the effect of the friction. In some examples, the method includes determining the rate of change includes determining a frequency of force or torque outputs of the actuator.

An example tangible article of manufacture storing machine readable instructions which, when executed, cause a machine to: determine a value corresponding to friction of an actuator and a process control device to be operated by the actuator; and determine a value indicative of an effect of the friction on operation of the process control device via the actuator based on the value corresponding to the friction and a predetermined value. In some examples, the effect of the friction on the operation of the process control device is a deterioration of a movement characteristic of a stem or shaft of the process control device in response to a force or torque applied by the actuator to the stem or shaft.

An example method includes determining a first force or torque corresponding to friction of a process control device and an actuator operatively coupled to the process control device via a stem or shaft; in response to the first force or torque, determining a first command to operate the process control device via the stem or shaft to obtain a first response of the actuator; determining a second force or torque corresponding to friction of the process control device and the actuator; and in response to the second force or torque, determining a second command to operate the process control device via the stem or shaft to obtain a second response of the actuator.

In some examples, determining the first response of the actuator to the first command includes comparing the first force or torque corresponding to the friction to an estimated force or torque. In some examples, the estimated force or torque is based on a difference between an estimated maximum force or torque of the actuator and an estimated force or torque of the actuator to perform an action. In some examples, the first response of the actuator corresponds to a movement characteristic of the stem or shaft in response to a force or torque applied to the stem or shaft by the actuator. In some examples, the movement characteristic is a sensitivity. In some examples, the movement characteristic is a preciseness. In some examples, the movement characteristic is a responsiveness. In some examples, the method includes sending an alert message when the first response or the second response of the actuator has deteriorated to or below a predetermined level.

In some examples, determining the first force or torque corresponding to the friction includes determining a difference between a force or torque applied by the actuator to the stem or shaft at a first position and a force or torque applied by the actuator to the stem or shaft at a second position during movement of the stem or shaft from the first position to the second position. In some examples, the second command is modified from the first command to compensate for differences between the first and second forces or torques.

An example tangible article of manufacture storing machine readable instructions which, when executed, cause a machine to: determine a force or torque corresponding to friction of a process control device and an actuator operatively coupled to the process control device via a stem or shaft; in response to the force or torque, determine a first command to operate the process control device via the stem or shaft to obtain a response of the actuator; determine a second force or torque corresponding to friction of the process control device and the actuator; and in response to the second force or torque, determine a second command to operate the process control device via the stem or shaft to obtain a second response of the actuator.

An example method includes determining a force or torque at a plurality of times during a continuous process control operation, the forces or torques corresponding to friction of a process control device and an actuator operatively coupled to the process control device via a stem or shaft; and in response to the forces or torques at the respective times, dynamically updating a command to operate the process control device via the stem or shaft to obtain a response of the actuator during the continuous process control operation.

In some examples, determining the response of the actuator to the command includes comparing the force or torque corresponding to the friction to an estimated force or torque. In some examples, the estimated force or torque is based on a difference between an estimated maximum force or torque of the actuator and an estimated force or torque of the actuator to perform an action. In some examples, the response of the actuator corresponds to a movement characteristic of the stem or shaft in response to a force or torque applied to the stem or shaft by the actuator. In some examples, the movement characteristic is one or more of a sensitivity, a preciseness, or a responsiveness. In some examples, the method includes sending an alert message when the response of the actuator has deteriorated to or below a predetermined level. In some examples, determining the force or torque corresponding to the friction includes determining a difference between a force or torque applied by the actuator to the stem or shaft at a first position and a force or torque applied by the actuator to the stem or shaft at a second position during movement of the stem or shaft from the first position to the second position.

Although certain example methods and apparatus have been described herein, the scope of coverage of this patent is not limited thereto. On the contrary, this patent covers all methods, apparatus and articles of manufacture fairly falling within the scope of the appended claims either literally or under the doctrine of equivalents.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. An apparatus, comprising:
   a housing;
   a processor disposed in the housing, the processor to:
      determine a first force or torque corresponding to friction of a process control device and an actuator operatively coupled to the process control device via a stem or shaft;
      in response to the first force or torque, determine a first command to operate the process control device via the stem or shaft to obtain a first response of the actuator;
      determine a second force or torque corresponding to friction of the process control device and the actuator; and
      in response to the second force or torque, determine a second command to operate the process control device via the stem or shaft to obtain a second response of the actuator.

2. The apparatus of claim 1, wherein the processor is to determine the first response of the actuator to the first command by comparing the first force or torque corresponding to the friction to an estimated force or torque.

3. The apparatus of claim 2, wherein the processor is to determine the estimated force or torque based on a difference between an estimated maximum force or torque of the actuator and an estimated force or torque of the actuator to perform an action.

4. The apparatus of claim 1, wherein the processor is to determine the first response of the actuator based on a movement characteristic of the stem or shaft in response to a force or torque applied to the stem or shaft by the actuator.

5. The apparatus of claim 4, wherein the movement characteristic includes one or more of a sensitivity, a preciseness, or a responsiveness.

6. The apparatus of claim 1, wherein the processor is to send an alert message when the first response or the second response of the actuator has deteriorated to or below a threshold level.

7. The apparatus of claim 1, wherein the processor is to determine the first force or torque corresponding to the friction by determining a difference between a force or torque applied by the actuator to the stem or shaft at a first position and a force or torque applied by the actuator to the stem or shaft at a second position during movement of the stem or shaft from the first position to the second position.

8. The apparatus of claim 1, wherein the processor is to modify the second command from the first command to compensate for differences between the first and second forces or torques.

9. An apparatus, comprising:
   a housing;
   a processor disposed in the housing, the processor to:
      determine a force or torque at a plurality of times during a continuous process control operation, the forces or torques corresponding to friction of a process control device and an actuator operatively coupled to the process control device via a stem or shaft; and in response to the forces or torques at the respective times, dynamically update a command to operate the process control device via the stem or shaft to obtain a response of the actuator during the continuous process control operation.

10. The apparatus of claim 9, wherein the processor is to determine the response of the actuator to the command by comparing the force or torque corresponding to the friction to an estimated force or torque.

11. The apparatus of claim 10, wherein the processor is to determine the estimated force or torque based on a difference between an estimated maximum force or torque of the actuator and an estimated force or torque of the actuator to perform an action.

12. The apparatus of claim 11, wherein the processor is to determine the response of the actuator based on a movement characteristic of the stem or shaft in response to a force or torque applied to the stem or shaft by the actuator.

13. The apparatus of claim 12, wherein the movement characteristic is one or more of a sensitivity, a preciseness, or a responsiveness.

14. The apparatus of claim 9, wherein the processor is to generate an alert message when the response of the actuator has deteriorated to or below a threshold level.

15. The apparatus of claim 9, wherein the processor is to determine the force or torque corresponding to the friction by determining a difference between a force or torque applied by the actuator to the stem or shaft at a first position and a force or torque applied by the actuator to the stem or shaft at a second position during movement of the stem or shaft from the first position to the second position.

* * * * *